United States Patent
McDaniel et al.

(10) Patent No.: US 8,449,617 B1
(45) Date of Patent: May 28, 2013

(54) CONVERTIBLE GLENOID IMPLANT

(75) Inventors: John McDaniel, Warsaw, IN (US);
Benjamin Heilman, Warsaw, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 0 days.

(21) Appl. No.: 13/297,631

(22) Filed: Nov. 16, 2011

(51) Int. Cl.
*A61F 2/40* (2006.01)

(52) U.S. Cl.
USPC .............. 623/19.13; 623/19.11; 623/19.12; 623/19.14

(58) Field of Classification Search
USPC .......... 623/19.13, 19.11, 19.12, 19.14, 23.41, 623/22.11, 22.15
See application file for complete search history.

(56) References Cited

U.S. PATENT DOCUMENTS

| | | | |
|---|---|---|---|
| 3,916,451 A | 11/1975 | Buechel et al. | |
| 6,228,119 B1 | 5/2001 | Ondrla et al. | |
| 6,514,287 B2 | 2/2003 | Ondrla et al. | |
| 6,599,321 B2 | 7/2003 | Hyde, Jr. | |
| 7,033,396 B2 | 4/2006 | Tornier | |
| 7,175,663 B1 | 2/2007 | Stone | |
| 7,445,638 B2 | 11/2008 | Beguin et al. | |
| 7,465,319 B2 | 12/2008 | Tornier | |
| 7,470,287 B2 | 12/2008 | Tornier et al. | |
| 7,608,109 B2 * | 10/2009 | Dalla Pria | 623/19.11 |
| 7,621,961 B2 | 11/2009 | Stone | |
| 7,753,959 B2 * | 7/2010 | Berelsman et al. | 623/19.11 |
| 2005/0261775 A1 | 11/2005 | Baum et al. | |
| 2006/0069443 A1 | 3/2006 | Deffenbaugh et al. | |
| 2006/0122705 A1 | 6/2006 | Morgan | |
| 2007/0244563 A1 | 10/2007 | Roche et al. | |
| 2009/0062923 A1 | 3/2009 | Swanson | |
| 2009/0118837 A1 | 5/2009 | Winslow et al. | |
| 2010/0114326 A1 | 5/2010 | Winslow et al. | |
| 2010/0161066 A1 * | 6/2010 | Iannotti et al. | 623/19.11 |
| 2010/0222886 A1 | 9/2010 | Wiley et al. | |
| 2011/0035013 A1 | 2/2011 | Winslow et al. | |
| 2011/0118846 A1 | 5/2011 | Katrana et al. | |

FOREIGN PATENT DOCUMENTS

| | | | |
|---|---|---|---|
| EP | 1639967 A1 | | 3/2006 |
| EP | 1782764 A2 | | 5/2007 |
| EP | 2243444 A1 | | 10/2010 |
| FR | 2652498 A1 | * | 4/1991 |
| FR | 2843293 A1 | | 2/2004 |

OTHER PUBLICATIONS

Michel Colombier et al., Modular Assembly for Shoulder Prosthesis (English Translation of FR 2652498 A1), Apr. 5, 1991, United Sates Patent and Trademark Office (Translated by the Ralph Mcelroy Translation Company), pp. 1-12.*
International Search Report and Written Opinion of the International Searching Authority for International Application No. PCT/US2012/064194, mailed Feb. 19, 2013.

* cited by examiner

*Primary Examiner* — Thomas J Sweet
*Assistant Examiner* — Krutanjali M Shah
(74) *Attorney, Agent, or Firm* — Harness, Dickey

(57) ABSTRACT

A shoulder implant assembly constructed in accordance to one example of the present disclosure includes a frame member, a cup, and a glenosphere. The frame member can have a central hub and a first arm extending therefrom. The frame member can be configured to selectively and alternatively couple with first shoulder implant components in a traditional shoulder configuration and with second shoulder implant components in a reverse shoulder configuration. The cup can have a concave surface that is configured to articulate with a humeral head component. The cup can be selectively coupled to the frame member in the traditional shoulder configuration. The glenosphere can have an outer articulating surface that is configured to articulate with a second cup. The glenosphere can be selectively coupled to the frame member in the reverse shoulder configuration.

18 Claims, 4 Drawing Sheets

CONVERTIBLE GLENOID IMPLANT

FIELD

The present disclosure relates to a shoulder implant assembly and a related method for converting a traditional shoulder implant to a reverse shoulder implant.

BACKGROUND

This section provides background information related to the present disclosure which is not necessarily prior art.

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of such a shoulder joint prosthesis becomes necessary, the natural head portion of the humerus may be resected and a cavity may be created in the intramedullary canal of the host humerus for accepting a humeral component. The humeral component may include a head portion used to replace the natural head of the humerus. Once the humeral component has been implanted, the glenoid cavity positioned at the glenoid may also be resurfaced and shaped to accept a glenoid component. The glenoid component generally includes an articulating surface which is engaged by the head portion of the humeral component. Such an implant configuration is generally referred to as a traditional shoulder configuration. In some instances, it may be necessary to convert the traditional shoulder configuration into a reverse shoulder configuration such as to achieve a higher level of constraint. In this regard, the humeral component and glenoid component may need to be removed and replaced with reverse shoulder components. When converting a traditional shoulder configuration to a reverse shoulder configuration, it is desirable to provide an efficient and minimally invasive transition on both the humeral side of the system and the glenoid side of the system.

SUMMARY

This section provides a general summary of the disclosure, and is not a comprehensive disclosure of its full scope or all of its features.

A shoulder implant assembly constructed in accordance to one example of the present disclosure includes a frame member, a first cup, and a glenosphere. The frame member can have a central hub and a first arm extending therefrom. The frame member can be configured to selectively and alternatively couple with first shoulder implant components in a traditional shoulder configuration and with second shoulder implant components in a reverse shoulder configuration. The first cup can have a concave surface that is configured to articulate with a humeral head component. The first cup can be selectively coupled to the frame member in the traditional shoulder configuration. The glenosphere can have an outer articulating surface that is configured to articulate with a second cup. The glenosphere can be selectively coupled to the frame member in the reverse shoulder configuration.

According to additional features, the shoulder implant assembly can further include a first peg configured to mate with the first arm of the frame member in the traditional shoulder configuration. The first peg can have an elongated body that extends a first distance. A first bone screw can be configured to mate with the first arm of the frame member in the reverse shoulder configuration. The first bone screw can have an elongated body that extends a second distance. The second distance can be greater than the first distance. The first arm can define a first receiving portion configured to selectively and alternatively receive the first peg in the traditional shoulder configuration and the first bone screw in the reverse shoulder configuration. The first receiving portion can include a first boss defining a first threaded aperture.

According to additional features, the first peg and the first bone screw can have threads formed thereon configured to threadably mate with the threaded aperture. The shoulder implant assembly can further comprise an adapter having a male tapered outer surface that is configured to be received into a complementary female tapered surface defined on the glenosphere. The adapter can define a throughbore configured to receive a central bone screw extending through the central hub in the reverse shoulder configuration. In one configuration, the first arm can be porous coated.

According to other features, the frame member can further include a second arm and a third arm that extend from the central hub. The first, second, and third arms can each include a receiving portion having a hub configured to selectively and alternatively receive a peg in the traditional shoulder configuration and a bone screw in the reverse shoulder configuration. The peg and the bone screw can have distinct lengths. In one configuration, the first, second, and third arms extend in a Y-shaped pattern.

A method of performing shoulder arthroplasty according to one example of the present teachings can include implanting a frame member into a glenoid. A first cup can be coupled to the frame member. The first cup can have a first concave articulating surface. A humeral component having a humeral head can be implanted into a humerus. The humeral head can be configured to articulate relative to the first concave articulating surface. The cup can be removed from the frame member subsequent to bone interdigitation with the frame member while leaving the frame member implanted in the glenoid. A glenosphere can be coupled to the frame member. The humeral head can be removed from the humeral component. A second cup can be coupled to the humeral component. The second cup can have a second concave articulating surface. The glenosphere can be configured to articulate relative to the second concave articulating surface.

According to additional features, the method can further comprise advancing a peg through a boss formed on an arm extending from a central hub of the frame member and into the glenoid. Coupling the glenosphere can include removing the peg from the boss and subsequently inserting a bone screw through the boss. The bone screw can penetrate into the glenoid a further distance as compared to the peg. The method can further include advancing a central peg through the central hub and into the glenoid. The central peg can be removed. An adapter can be coupled to the glenosphere. A central bone screw can be inserted through the adapter and into the glenoid.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
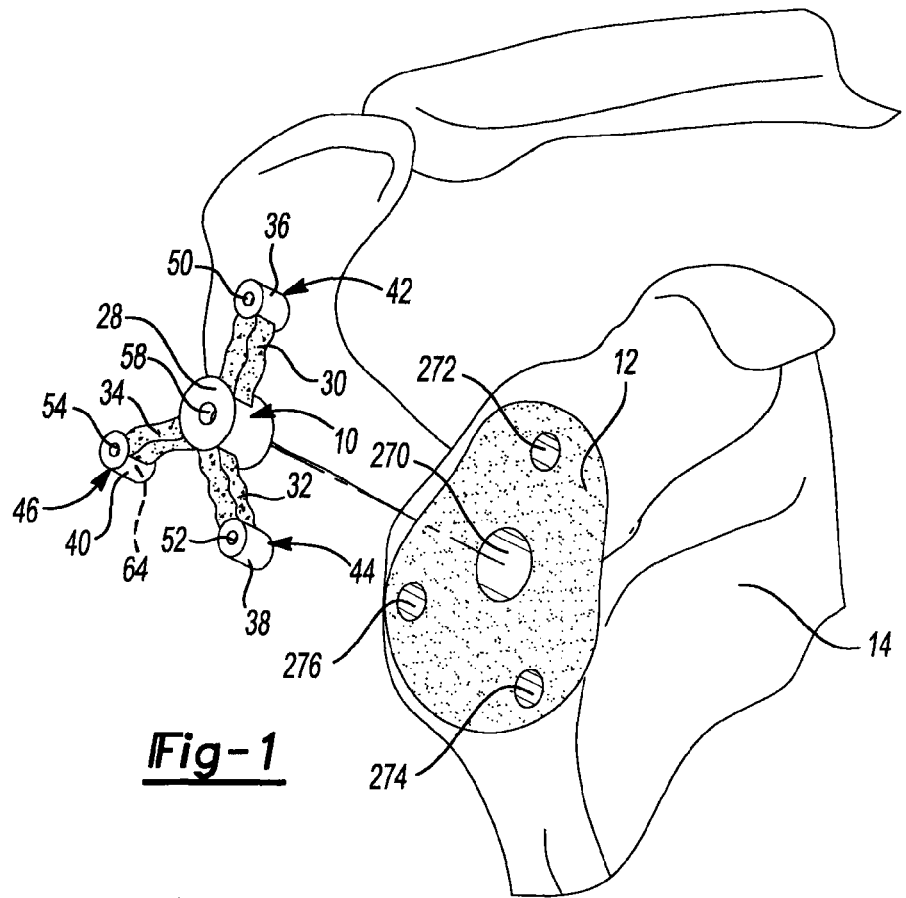
FIG. 1 is a front perspective view of a frame member constructed in accordance to one example of the present teachings and shown adjacent a right glenoid cavity.
Figure 3:
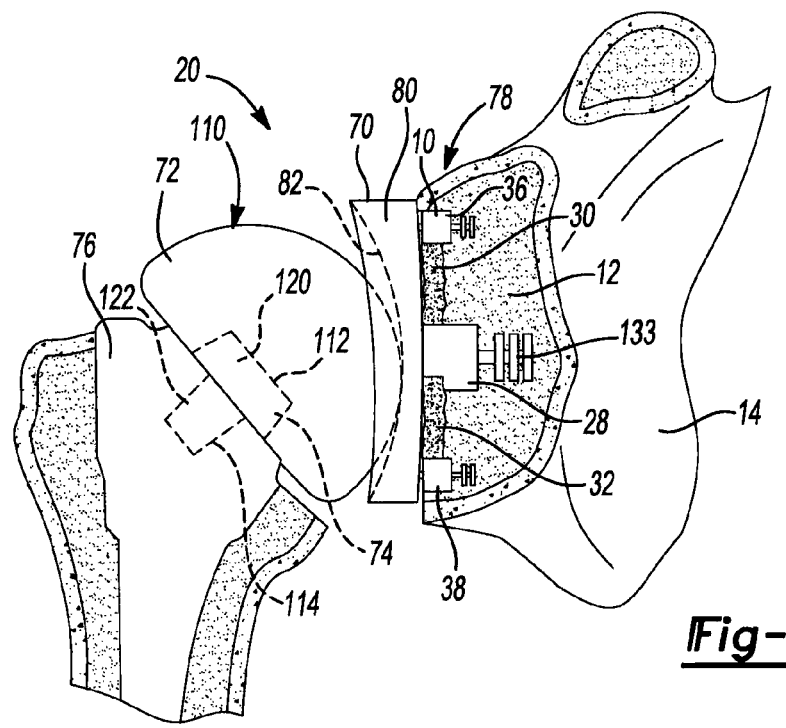
FIG. 3 is a side view of the frame member of FIG. 1 shown implanted as part of a traditional shoulder implant assembly.
Figure 8:
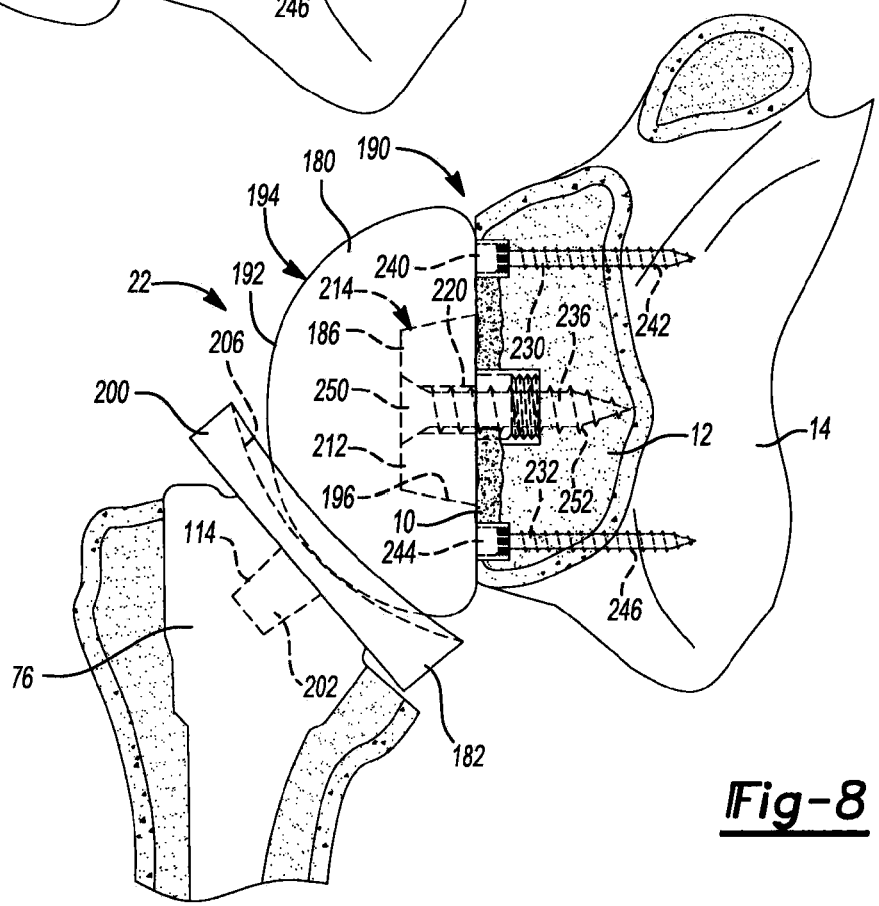
FIG. 8 is a side view of the reverse shoulder implant assembly shown in an implanted position.

With initial reference now to FIGS. 1, 3, and 8, a frame member constructed in accordance to one example of the present teachings is shown and generally identified at reference numeral 10. As will become appreciated from the following discussion, the frame member 10 is configured to be implanted into a glenoid cavity 12 of a scapula 14 as part of either a traditional shoulder implant assembly 20 (FIG. 3) or a reverse shoulder implant assembly 22 (FIG. 8). More particularly, the frame member 10 is configured to be implanted into the glenoid cavity 12 as part of a traditional shoulder implant assembly and remain implanted in the glenoid cavity 12 as part of a reverse shoulder implant assembly. In this regard, the frame member 10 can remain implanted and relatively undisturbed during a transition from converting a traditional shoulder implant into a reverse shoulder implant as will become appreciated from the following discussion.

Figure 2:
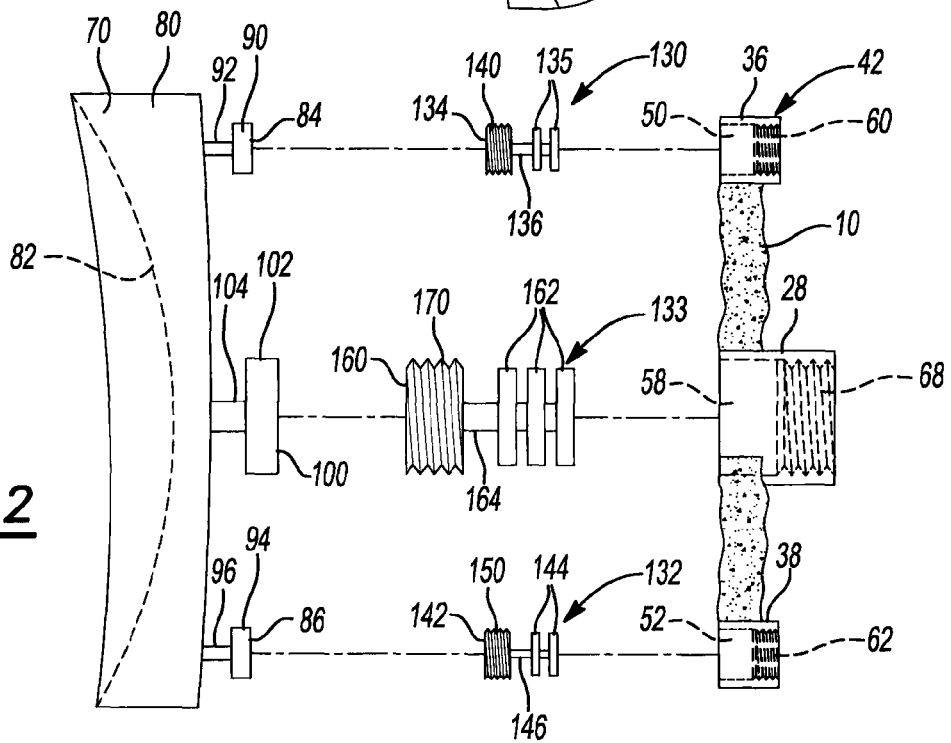
FIG. 2 is an exploded side view of the frame member of FIG. 1 and shown as part of a traditional shoulder implant assembly including a series of pegs configured to couple with a first cup according to one configuration.

With particular reference now to FIGS. 1 and 2, the frame member 10 will be described in greater detail. The frame member 10 generally includes a central hub 28 having a first arm 30, a second arm 32, and a third arm 34 extending therefrom. The first arm 30 includes a first boss 36 formed on a terminal end thereof. The second arm 32 includes a second boss 38 formed on a terminal end thereof. The third arm 34 includes a third boss 40 formed on a terminal end thereof. The first, second, and third bosses 36, 38, and 40 provide first, second, and third receiving portions 42, 44, and 46, respectively. The first receiving portion 42 has a first bore 50 defined through the first boss 36. The second receiving portion 44 has a second bore 52 defined through the second boss 38. The third receiving portion 46 defines a third bore 54 defined through the third boss 40. The central hub 28 defines a central bore 58. The frame member 10 can be formed of biocompatible material such as titanium for example.

The first boss 36 can include first threads 60. The second boss 38 can include second threads 62 thereon. The third boss 40 can include third threads 64 thereon. The central hub 28 can have central threads 68 formed thereon. The first, second, and third arms 30, 32, and 34 can be formed of porous material or have porous material disposed thereon.

Turning now to FIG. 3 with continued reference to FIG. 2, the traditional shoulder implant assembly 20 will be further described. The traditional shoulder implant assembly 20 generally includes the frame member 10, a first cup 70, a humeral head 72, an adapter 74, a humeral stem 76, and a collection of first fasteners 78. The first cup 70 generally includes a cup body 80 that defines a concave articulating surface 82. The cup body 80 can have a first leg 84, a second leg 86, and a third leg (not specifically shown). The first leg 84 can include a distal connecting end 90 extending from a post 92. The second leg 86 can have a distal connecting end 94 extending from a post 96. A central leg 100 having a distal connecting end 102 extending from a peg 104.

The humeral head 72 has an articulating surface 110 that is configured to articulate relative to the concave articulating surface 82 of the first cup 70. The humeral head 72 can further include a female tapered receiving portion 112. The humeral stem 76 can define a female tapered receiving portion 114. The adapter 74 generally includes a first male taper 120 and a second male taper 122. The first and second male tapers 120 and 122 are each generally cylindrical. The first male taper 120 can have a larger diameter than the second male taper 122. The first male taper 120 can be angled to cooperate with the corresponding female tapered receiving portion 112 of the humeral head 72. The second male taper 122 is angled to cooperate with the female tapered receiving portion 114 of the humeral stem 76. In one example, the respective first and second male tapers 120 and 122 can create a Morse taper lock with the complementary female tapered receiving portions 112 and 114, respectively.

The first fasteners 78 can generally include a first peg 130, a second peg 132, a central peg 133, and a third peg (not specifically shown). The first peg 130 includes a first head 134 and a pair of radial flanges 135 extending from a longitudinal shaft 136. The first head 134 can include threads 140 formed thereon. The second peg 132 can include a second head 142 and a pair of radial flanges 144 that extend from a shaft 146. The second head 142 can include threads 150 thereon. The central peg 133 generally includes a head 160 and a series of radial flanges 162 that extend from an elongated shaft 164. The head 160 can include threads 170 thereon. The first fastener 78 can be formed of ultra high molecular weight polyethylene (UHMWPE) or other suitable material. It is further appreciated that the particular geometry and configurations of the pegs is merely exemplary and other fasteners such as bone screws may be used.

Figure 4:
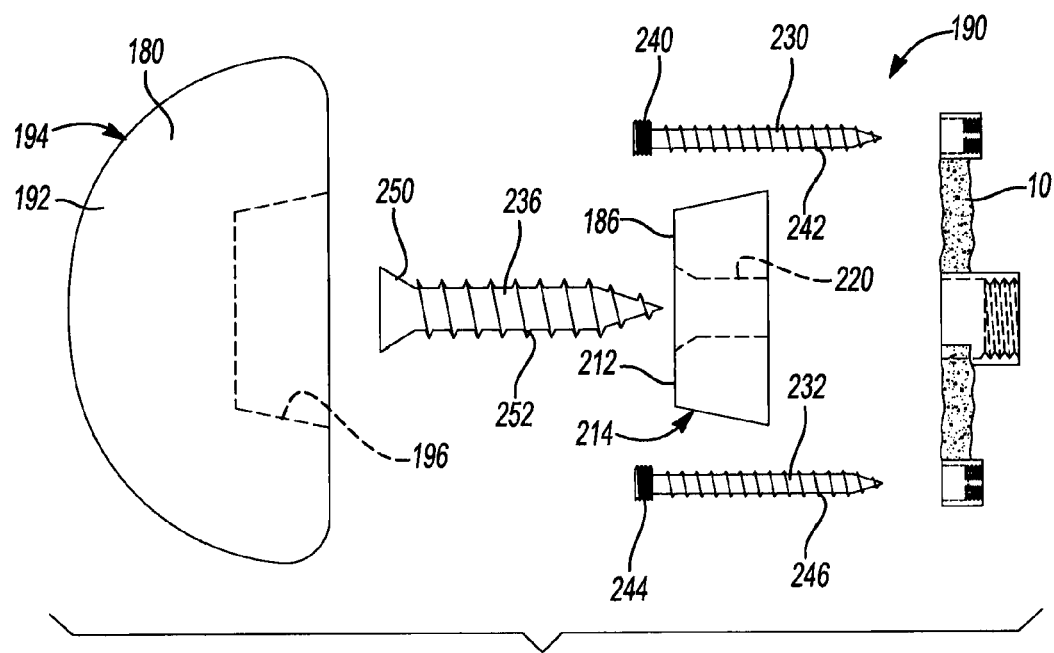
FIG. 4 is an exploded perspective view of the frame member shown as part of a reverse shoulder implant assembly including an adapter, a series of bone screws, and a glenosphere according to one example.

With reference now to FIGS. 4 and 8, the reverse shoulder implant assembly 22 will be further described. The reverse shoulder implant assembly 22 can generally include the frame member 10, a glenosphere 180, a second cup 182, the humeral stem 76, an adapter 186, and a series of second fasteners 190. The glenosphere 180 generally includes a body 192 having an outer articulating surface 194 and defines a female tapered receiving portion 196. The second cup 182 can include a second cup body 200 that includes a male tapered portion 202 configured to cooperatively mate with the female tapered receiving portion 114 of the humeral stem 76. The second body 200 of the second cup 182 further includes a concave articulating surface 206 that is configured to articulate with the outer articulating surface 194 of the glenosphere 180. The adapter 186 generally includes an adapter body 212 having an outer tapered surface 214. The adapter 186 defines a throughbore 220.

The second fasteners 190 can generally include a first bone screw 230, a second bone screw 232, a third bone screw (not specifically shown), and a central bone screw 236. The first bone screw 230 can include a threaded head 240 and a threaded shank 242. The second bone screw 232 can include a threaded head 244 and a threaded shank 246. The central bone screw 236 can include a tapered head 250 and threaded shank 252. The second fasteners 190 are merely exemplary. It will be appreciated that other fasteners may be used. In the present example, the second fasteners 190 are longer in axial length than the first fasteners 78 to penetrate deeper into the bone of the glenoid cavity 12.

One method of implanting the traditional shoulder implant assembly 20 according to one example of the present teachings will now be described. Once the glenoid cavity 12 has been sufficiently reamed, a surgeon can prepare a central bore 270, a first hole 272, a second hole 274, and a third hole 276 into the glenoid cavity 12 (FIG. 1). It will be appreciated that the first, second, and third bores 50, 52, and 54 may be used as a reference in determining the location of the respective holes 272, 274, and 276. Next, the frame member 10 can be positioned onto the glenoid cavity 12 and the first peg 130, second peg 132 and third peg (not shown) can be inserted into the first bore 50, second bore 52 and third bore 54, respectively of the frame member 10. In this regard, respective flanges 135 and 144 as well as the flanges from the third peg (not shown) are inserted into the bone of the glenoid cavity 12. At this point, the central peg 133 can be located into the central bore 58. The radial flanges 162 can be caused to be inserted into the bone of the glenoid cavity 12. The first cup 70 can then be located into the first, second, and third receiving portions 42, 44, and 46. Specifically, the respective distal connecting ends 90 and 94 of the legs 84 and 86 can be located partially into the respective first and second bores 50 and 52 via snap-fit or other means. The third connecting end from the third peg (not shown) may also concurrently be located partially into the third bore 54. The humeral head 72 can then be coupled to the humeral stem 76 by way of the adapter 74.

As identified above, in some examples, it may become necessary to convert the traditional shoulder implant assembly 20 (FIG. 3) into the reverse shoulder implant assembly 22 (FIG. 8). According to the present disclosure, the frame member 10 can remain implanted into the glenoid cavity 12 during the conversion from the traditional shoulder implant assembly 20 to the reverse shoulder implant assembly 22. In this regard, the frame member 10 can take advantage of any bone that has interdigitated into the porous surface of the respective first, second, and third arms 30, 32, and 34. Moreover, the conversion can be minimally invasive as the frame member 10 can remain relatively undisturbed and implanted in the bone of the glenoid cavity 12.

Figure 5:
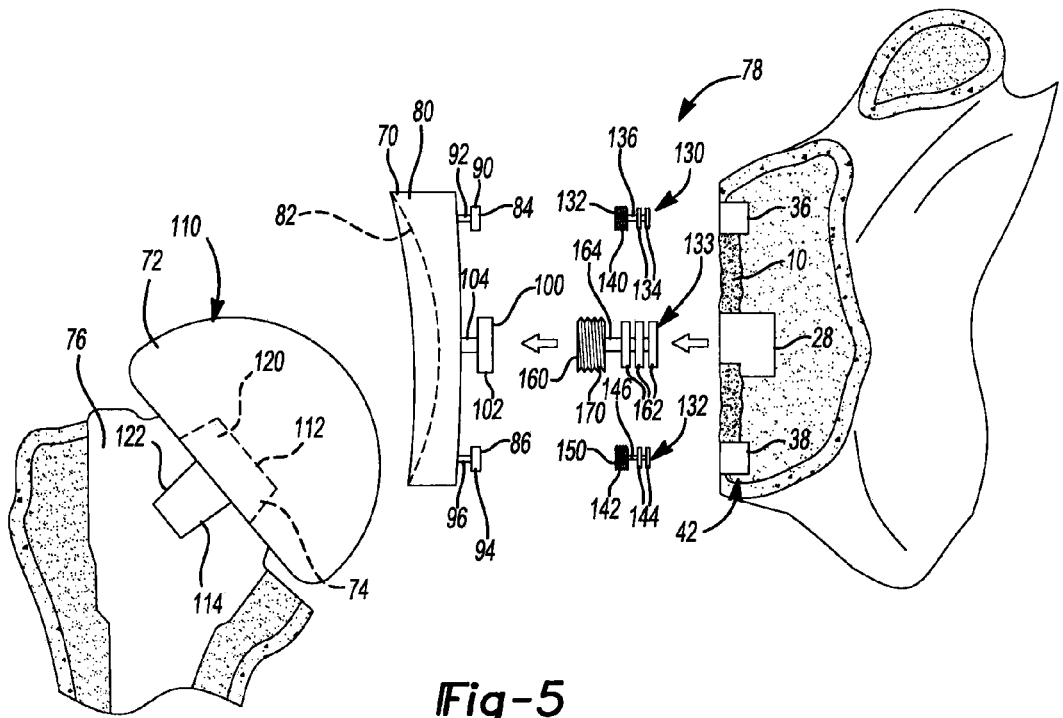
FIG. 5 is a partial exploded perspective view of the traditional shoulder implant assembly being removed from the glenoid while leaving the frame member implanted.
Figure 6:
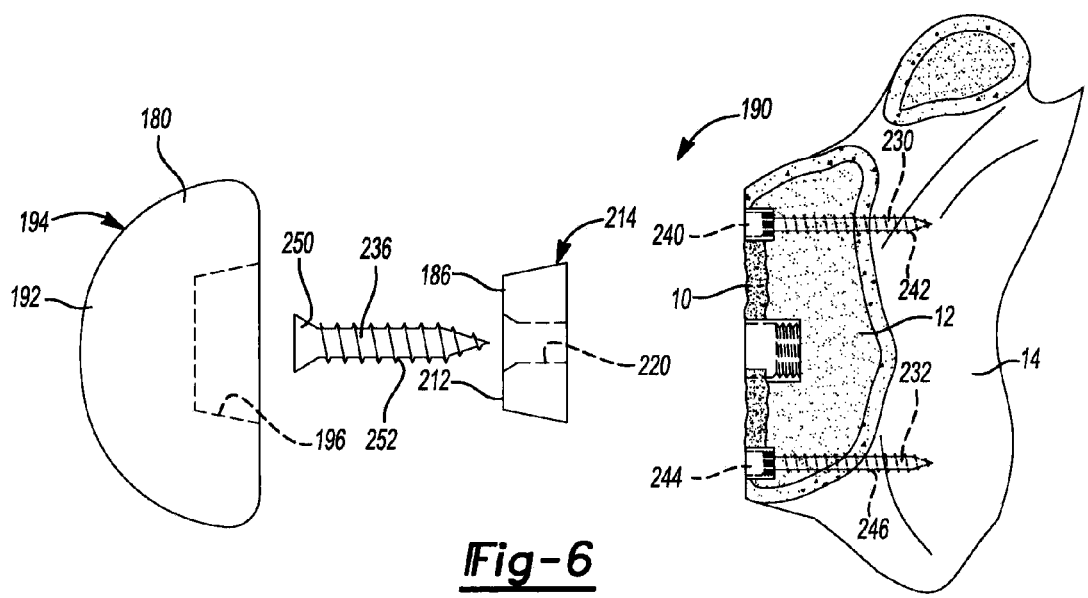
FIG. 6 is an exploded perspective view of the glenosphere and adapter of FIG. 4 aligned for coupling to the frame member.
Figure 7:
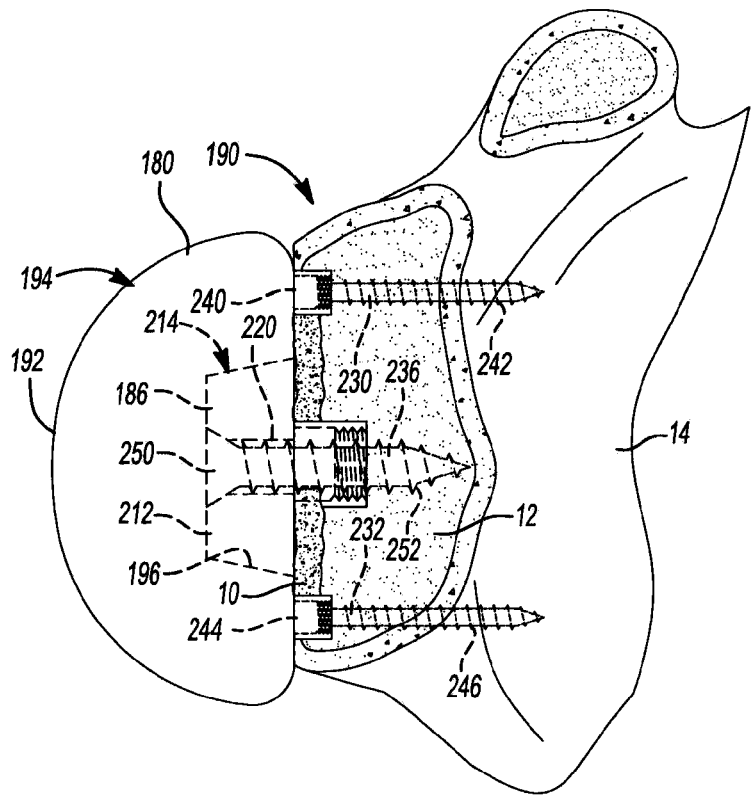
FIG. 7 is a side view of the glenosphere coupled relative to the frame member in the reverse shoulder configuration.

Turning now to FIG. 5, the first cup 70 and the first fasteners 78 are then removed from the frame member 10. Next, as viewed from FIGS. 6-8, the first bone screw 230, the second bone screw 232, and the third bone screw of the second fasteners 190 can be driven through the respective first, second, and third bores 50, 52, and 54. The central bone screw 236 can then be inserted into the throughbore 220 of the adapter 186 and located into the central bore 58. The threaded shank 252 of the central bone screw 236 can be driven into the bone of the glenoid cavity 12. The threads 242 and 246 of the bone screws 230 and 232 can likewise be driven into the bone of the glenoid cavity 12. The glenosphere 180 can then be located relative to the adapter 186. Specifically, the tapered surface 214 of the adapter 186 can be located into the female tapered receiving portion 196 of the glenosphere 180. The male tapered portion 202 of the second cup 182 can then be inserted into the female tapered receiving portion 114 after the humeral head 72 and adapter 74 have been removed from the humeral stem 76.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A shoulder implant assembly comprising:
a frame member having a central hub a frame member having a central hub and a first arm extending outwardly in a radial direction from a central axis of the central hub, wherein the frame member is a single component that is configured to selectively and alternatively couple with first shoulder implant components in a traditional shoulder configuration and with second shoulder implant components in a reverse shoulder configuration;
a first cup having a concave surface configured to articulate with a humeral head component, wherein the first cup is selectively and directly coupled to the frame member in the traditional shoulder configuration; and
a glenosphere having an outer articulating surface configured to articulate with a second cup, wherein the glenosphere is selectively and directly coupled to the frame member in the reverse shoulder configuration.

2. The shoulder implant assembly of claim 1, further comprising:
a first peg configured to mate with the first arm of the frame member in the traditional shoulder configuration, the first peg having an elongated body that extends a first distance; and
a first bone screw configured to mate with the first arm of the frame member in the reverse shoulder configuration, the first bone screw having an elongated body that extends a second distance, wherein the second distance is greater than the first distance.

3. The shoulder implant assembly of claim 2 wherein the first arm defines a first receiving portion configured to selectively and alternatively receive the first peg in the traditional shoulder configuration and the first bone screw in the reverse shoulder configuration.

4. The shoulder implant assembly of claim 3 wherein the first receiving portion includes a first boss defining a first threaded aperture.

5. The shoulder implant assembly of claim 4 wherein the first peg and the first bone screw have threads formed thereon configured to threadably mate with the threaded aperture.

6. The shoulder implant assembly of claim 1, further comprising an adapter having a male tapered outer surface configured to be received into a complementary female tapered surface defined on the glenosphere.

7. The shoulder implant assembly of claim 6 wherein the adapter defines a throughbore configured to receive a central bone screw extending through the central hub in the reverse shoulder configuration.

8. The shoulder implant assembly of claim 1 wherein the first arm is porous coated.

9. The shoulder implant assembly of claim 1 wherein the frame member further includes a second arm and a third arm extending from the central hub, wherein the first, second and third arms each include a receiving portion having a hub configured to selectively and alternatively receive a peg in a traditional shoulder configuration and a bone screw in the reverse shoulder configuration, wherein the peg and the bone screw have distinct lengths.

10. The shoulder implant assembly of claim 9 wherein the first, second and third arms extend in a Y-shaped pattern.

11. The shoulder implant assembly of claim 1 wherein the first cup has a first distal connecting end extending away from the central hub and that is received and engaged by a receiving portion on the first arm in a snap-fit relationship in the traditional shoulder configuration.

12. A shoulder implant assembly comprising:
a frame member having first, second and third arms extending outwardly in a radial direction from a central axis of a central hub, wherein each of the first second and third arms includes a boss defining a bore, wherein the frame member is a single component that is configured to be implanted into a glenoid and selectively and alternatively couple with first shoulder implant components in a traditional shoulder configuration and with second shoulder implant components in a reverse shoulder configuration;
a first cup having a concave surface configured to articulate with a humeral head component, wherein the first cup is selectively and directly coupled to the frame member in the traditional shoulder configuration;
a glenosphere having an outer articulating surface configured to articulate with a second cup, wherein the glenosphere is selectively and directly coupled to the frame member in the reverse shoulder configuration;
a series of first fasteners each having an elongated body extending a first length between a first end and a second end, the first end configured to be at least partially received by the respective bosses and the second end configured to couple and directly engage the cup in the traditional shoulder configuration; and
a series of second fasteners each having an elongated body extending a second length between a first end and a second end, the first end configured to be at least partially received by the respective bosses in the reverse shoulder configuration, wherein the second length is greater than the first length.

13. The shoulder implant assembly of claim 12 wherein the series of first fasteners each have a plurality of radial flanges extending from the elongated body.

14. The shoulder implant assembly of claim 12 wherein each of the first fasteners are threaded at the first end and wherein the bore of each respective boss is threaded, wherein the first fasteners are configured to threadably mate with the respective bosses in the traditional shoulder configuration.

15. The shoulder implant assembly of claim 12, further comprising an adapter having a male tapered outer surface configured to be received into a complementary female tapered surface defined on the glenosphere.

16. The shoulder implant assembly of claim 15 wherein the adapter defines a throughbore configured to receive a central bone screw extending through the central hub in the reverse shoulder configuration.

17. The shoulder implant assembly of claim 12 wherein the first, second and third arms are porous coated.

18. The shoulder implant assembly of claim 12 wherein the first cup has a first, second and third distal connecting end extending from the central hub, wherein the first, second and third distal connecting ends are received and engaged by a first, second and third receiving portion on the first, second and third arms, respectively in the traditional shoulder configuration.

\* \* \* \* \*